United States Patent [19]

Campbell

[11] 4,000,205

[45] Dec. 28, 1976

[54] PURIFICATION OF FEED GAS STREAMS CONTAINING FERRIC CHLORIDE IN OXYCHLORINATION

[75] Inventor: Ramsey G. Campbell, Berkeley, Calif.

[73] Assignee: Stauffer Chemical Company, Westport, Conn.

[22] Filed: July 14, 1975

[21] Appl. No.: 595,464

[52] U.S. Cl. .................... 260/658 R; 260/654 A; 260/659 A; 423/488
[51] Int. Cl.² ........................................ C07C 17/00
[58] Field of Search ....... 260/658 R, 654 A, 659 A; 423/488

[56] References Cited

UNITED STATES PATENTS

| | | | |
|---|---|---|---|
| 3,461,084 | 8/1969 | Li | 260/658 R |
| 3,624,170 | 11/1971 | Wakiyama | 260/659 A |
| 3,657,367 | 4/1972 | Blake et al. | 260/658 R |

*Primary Examiner*—Delbert E. Gantz
*Assistant Examiner*—Joseph A. Boska
*Attorney, Agent, or Firm*—Joel G. Ackerman

[57] ABSTRACT

Ferric chloride is removed from gas streams containing the same by passing the stream through a bed of activated alumina impregnated with potassium chloride or sodium chloride.

4 Claims, No Drawings

PURIFICATION OF FEED GAS STREAMS CONTAINING FERRIC CHLORIDE IN OXYCHLORINATION

BACKGROUND OF THE INVENTION AND PRIOR ART

This invention relates to the removal of ferric chloride from gases containing the same. The removal of ferric chloride from gases may be necessary or desirable for any of several reasons.

For instance, certain chlorinated hydrocarbons, such as chloroform, carbon tetrachloride, 1,2-dichloroethane and ethyl chloride, are frequently produced by oxychlorination of corresponding saturated or unsaturated aliphatic hydrocarbons and/or their chlorinated derivatives. Such processes are carried out by contacting the hydrocarbon (e.g. methane, ethane, ethylene) with or without the presence of chlorinated derivatives thereof, with hydrogen chloride and an oxygen-containing gas (usually air) in the presence of a catalyst. In many oxychlorination processes, the catalyst comprises cupric chloride, plus additives such as alkali metal chlorides and/or rare earth metal chlorides, on a porous support such as alumina, silica-alumina, diatomaceous earth, etc. Such a cupric chloride oxychlorination catalyst may contain as minor impurities, small amounts of iron, for example, up to about 800 ppm. These impurities may be in the form of ferric chloride and/or other iron compounds. Additional amounts of iron chlorides (ferric and/or ferrous chloride, which would be converted to ferric chloride in the oxychlorination zone) may be introduced into the catalyst in the hydrogen chloride stream, resulting from hydrogen chloride corrosion of steel equipment or conduit lines in the hydrogen chloride flow circuit. Even stainless steel may corrode to some extent. Similarly, corrosion of steel piping and/or other equipment in the air system would produce small amounts of iron oxides which could also be converted to ferric chloride in the oxychlorination zone. Though ferric chloride has been proposed as an oxychlorination catalyst, it has been found that its presence can be detrimental to the performance of a cupric chloride catalyst in such a process, in that the presence of ferric chloride can result in catalyst disintegration and/or deactivation. These can result, for instance, in pressure drop increases, catalyst attrition due to formation of dust or catalyst fines, and a general shortening of catalyst life and lowering of activity. As small an increase as 0.1% of ferric chloride content in the catalyst (over such impurities as may be present) can have a deleterious effect on a cupric chloride catalyst which has otherwise been found satisfactory for oxychlorination reactions. The problem can be generally circumvented by fabricating the gaseous feed piping circuit and associated equipment from relatively noncorrosive materials such as nickel; however, this can be expensive, especially for large-volume equipment.

In other environments, various gases may contain amounts of ferric chloride resulting, for example, from corrosion of steel equipment, entrainment of ferric chloride particles in processes using ferric chloride catalysts, steel-making processes, etc. Depending on the particular process involved, it may be desired either to purify a gas containing ferric chloride so as to obtain a purified product or to remove the ferric chloride in order to prevent problems downstream of its introduction into the system.

Ferric chloride may also be present in process gases in the production of chlorides of metals such as titanium, tantalum, niobium and hafnium from ores containing iron compounds in addition to compounds of the desired metals. One process for removing ferric chloride from a gaseous mixture of metal chlorides is described in U.S. Pat. No. 3,066,010, and consists of passing the gases through a bed of hot rock salt. Ferric chloride forms a complex with the sodium chloride; the rock salt is heated to a temperature above the melting point of the complex (specifically 250°–450° C) to permit removal of the complex in molten form.

It is an object of the present invention to provide a process for the purification of gases containing ferric chloride.

A further object of the present invention is to provide a process for the purification of gases containing minor amounts of ferric chloride.

A still further object of the present invention is to provide a process for the removal of ferric chloride from hydrogen chloride gases.

Yet a further object of the present invention is to provide a process for the prevention of ferric chloride contamination of cupric chloride oxychlorination catalysts.

SUMMARY OF THE INVENTION

In brief, the invention herein comprises conducting a gas containing ferric chloride through a bed of activated alumina particles, which particles have been impregnated with a member selected from the group consisting of potassium chloride and sodium chloride.

DETAILED DESCRIPTION OF THE INVENTION

Ferric chloride is removed from gas streams containing the same by passing these streams through a bed comprising activated alumina which has been impregnated with potassium chloride and/or sodium chloride. Potassium chloride is preferred. In a preferred embodiment, the activated alumina is in the form of spherical particles. It has been found that the use of such particles results in a lower and more stable pressure drop through the system over an extended period of time and in addition, the alumina particles will possess a longer life. The bed will generally contain between about 5 and about 25 weight % of the chloride, preferably between about 10 and about 22 weight %. The impregnation is done by conventional techniques for impregnating alumina with an alkali metal halide. For instance, the pore volume of a high surface area alumina (preferably composed of spherical particles) is determined by heating the alumina (e.g. at 140°–160° C) to drive off water, cooling, immersing in water and reweighing to determine the amount of water absorbed (water pore volume of the alumina). Impregnation is conducted in a rotating vessel using the desired amount of metal chloride dissolved in an amount of water sufficient to form a solution having about 95–97% of the water pore volume as previously determined. The impregnated alumina is then dried and cooled.

The metal chloride-impregnated alumina can be situated as physically necessary in the system involved. For instance, it may be included as a filter in a gas transmission conduit. It may be included as a bed in the top section of a reactor, underneath which is a catalytic bed which could be adversely affected by the presence of ferric chloride. If the reactor is a tubular reactor, the metal chloride-impregnated alumina particles can be placed in the upper portions of the individual tubes. Thus, in an oxychlorination process, for instance, the hydrogen chloride feed can be passed through these particles before being mixed with the other reactants, or the combined feed stream of hydrogen chloride, hydrocarbon and oxygen-containing gas can first be passed through the impregnated alumina. In an oxychlorination process, this metal chloride-impregnated alumina, when located in the oxychlorination zone, will be effective in preventing contamination of the catalyst by ferric chloride formed in this zone from ferrous chloride, iron oxides or other iron compounds in that this metal chloride-impregnated alumina can furnish sites for reaction of such compounds with hydrogen chloride and/or chlorine to produce ferric chloride, which will be retained by the impregnated alumina. Such a situation is contemplated by me as being within the definition of the term "removing ferric chloride from a gaseous stream" as used in this application.

If the impregnated alumina bed is in close proximity to a catalyst which may be deactivated by the presence of ferric chloride, a suitable screen or perforated plate may be inserted between the alumina and the catalyst if desired, to prevent migration of ferric chloride-containing particles into the catalyst bed. Herein lies one advantage to the present invention over the process of U.S. Pat. No. 3,066,010: it can be utilized in a process without requiring additional equipment. Installation of a bed of rock salt inside the oxychlorination reactor would be impractical as the molten ferric chloride-sodium chloride mixture would flow down into the catalyst. In addition, in some processes, utilization of the process of the said U.S. patent would increase the overall process heat requirements since the rock salt must be continuously heated. The present invention, however, does not require such a heat input.

The alumina plus alkali metal halide as described herein can be effective in removing even minute amounts of ferric chloride from gaseous streams. For instance, referring again to an oxychlorination process, the ferric chloride content of the hydrogen chloride stream may be quite small, even less than 1 ppm. However, even such a small amount can, in a constant plant operation, readily build up to a concentration which adversely affects a cupric chloride catalyst.

Certain modifications and variations of the foregoing may be readily suggested to those skilled in the art. The foregoing description being illustrative, therefore, the invention is not to be taken as being limited thereto, but only by the claims which follow.

I claim:

1. In a process for oxychlorination of an aliphatic hydrocarbon and/or a chlorinated derivative thereof, in which the hydrocarbon and/or its chlorinated derivative is contacted with a hydrogen chloride stream containing ferric chloride and an oxygen containing gas in the presence of a catalyst comprising cupric chloride, which is subject to disintegration and/or deterioration in the presence of ferric chloride, the improvement comprising passing at least the hydrogen chloride stream, prior to its being brought into contact with the catalyst comprising cupric chloride, through a bed consisting essentially of activated alumina impregnated with a member of the group consisting of potassium chloride and sodium chloride.

2. A process accoording to claim 1 in which the total oxychlorination feed is passed through the bed prior to being brought into contact with the catalyst comprising cupric chloride.

3. A process according to claim 1 in which the alumina is impregnated with potassium chloride.

4. A process according to claim 1 in which the alumina is impregnated with sodium chloride.

* * * * *